United States Patent [19]

Soproni et al.

[11] Patent Number: 5,015,240
[45] Date of Patent: May 14, 1991

[54] HYPODERMIC NEEDLE SHIELD

[75] Inventors: Zoltan Soproni; Joseph A. Charmasson, both of San Diego, Calif.

[73] Assignee: Ian Campbell Cree, Shelburne, Canada

[21] Appl. No.: 517,326

[22] Filed: May 1, 1990

[51] Int. Cl.⁵ .............................................. A61M 5/32
[52] U.S. Cl. ..................................... 604/192; 604/263
[58] Field of Search ................ 604/198, 263, 192, 187

[56] References Cited

U.S. PATENT DOCUMENTS

| | | | |
|---|---|---|---|
| 3,134,380 | 5/1964 | Armao | 604/198 |
| 3,340,869 | 9/1967 | Bane | |
| 3,929,165 | 12/1975 | Diebolt et al. | 138/121 |
| 4,492,313 | 1/1985 | Touzani | 215/1 C |
| 4,725,267 | 2/1988 | Vaillancourt | 604/198 |
| 4,773,458 | 9/1988 | Touzani | 150/55 |
| 4,850,996 | 7/1989 | Cree | 604/198 |

Primary Examiner—John D. Yasko
Attorney, Agent, or Firm—Henri J. A. Charmasson

[57] ABSTRACT

A safety retractable sheath covers an injection needle for protection against accidental pricking. The sheath extends from a base secured to the hub of the needle and has bellowed walls made of resilient material. It may be axially retracted toward the hub to expose the needle, and springs back to cover its entire length when released. A constricted section of the sheath beyond the tip of the needle is axially offset to prevent accidental exposure of the tip. A latching bellow segment surrounding the base allows for adjustment of the sheaths to the lengths of the needle.

9 Claims, 1 Drawing Sheet

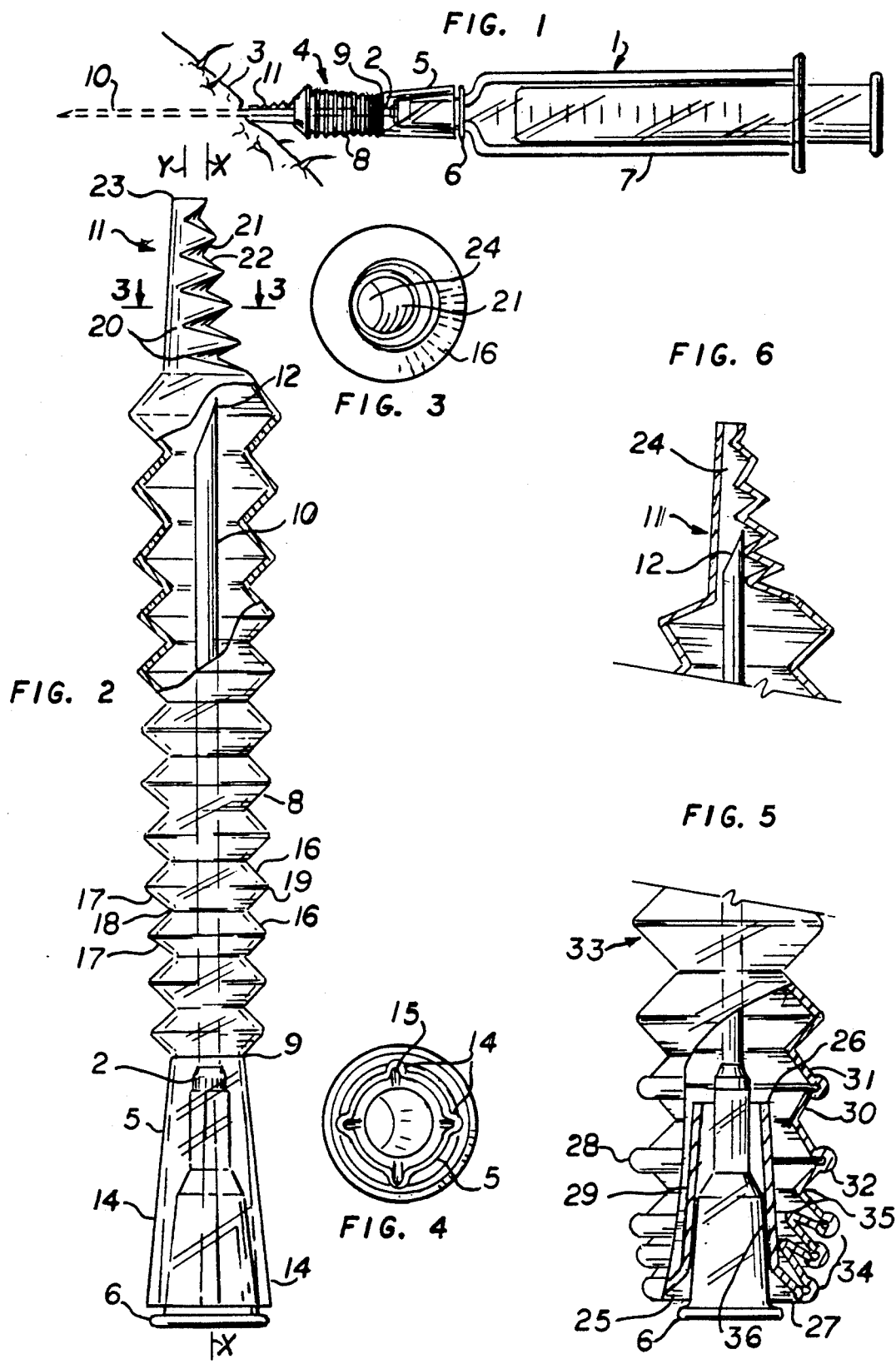

HYPODERMIC NEEDLE SHIELD

FIELD OF THE INVENTION

This invention relates to medical equipment and more specifically to injection needles.

BACKGROUND OF THE INVENTION

The hollow-pointed stainless steel needle in combination with syringes and infusion pumps is the common tool used in the healing arts to invade the body when giving injections or withdrawing body fluids. The sharply pointed end of a needle is extremely dangerous, and accidental pricking is very common even among nurses and other trained personnel. If accidental pricking occurs after the needle has been extracted from a patient with contaminated body fluid, the patient's disease may be transmitted to the treating physician or nurse. Procedures have been established for the recapping and safe disposal of medical needles immediately after their use. But the recapping process itself can be hazardous especially when occurring in the traumatic surroundings of a first aid treatment at the site of an accident or in the context of an emergency room intervention. Various automatic recapping systems have been devised in the past of which a typical example is disclosed in U.S. Pat. No. 4,850,996 Cree. In such case a retractable rigid tube surrounding the needle is biased by a coil spring which is collapsed when the tip of the sheath is brought into contact with the skin of the patient. The needle moves axially within the sheaths until it emerges at the distal end to penetrate the patient's tissue. This type of protective device is relatively complex and expensive to manufacture due to its multitude of components. It also does not provide a safe and automatic locking of the needle within the protective sheaths after use. Accordingly, there is a need for a simple and more effective way to automatically shield the tip of a medical needle after it has been withdrawn from the body of a patient.

SUMMARY OF THE INVENTION

The principal and secondary objects of this invention are:
- to provide a simple but effective retractable sheath for medical needles which can be formed as a single component;
- to provide a universal protective sheath that can be adapted to a variety of types and sizes of needles;
- to provide some protection against the accidental retracting of the sheaths after the needle has been withdrawn from a patient's body; and
- to provide sheaths which constitute a minimum interference with the use of the needle under a variety of circumstances.

These and other objects are achieved by a collapsible sheath which extends from a base attachable to the hub of a needle to cover the pointed tip of the needle. The sheath is made of a succession of bellowed sections which collapse to a very short length near the hub of the needle. The distal aperture through which the needle emerges is axially offset from the axis of the needle and sheath, so that when the sheath is expanded after use, the misalignment between the aperture and the needle tip prevents the accidental reappearance of the latter.

BRIEF DESCRIPTION OF THE DRAWING

FIG. 1 illustrates a syringe and needle assembly equipped with the invention in the process of an injection;

FIG. 2 is an elevational view of a first embodiment of the invention with a partial cut-out showing the internal structure;

FIG. 3 is a cross-sectional view taken along line 3—3 of FIG. 2;

FIG. 4 is a proximal end view of the sheaths;

FIG. 5 is a partial cross-sectional view of a second embodiment of the sheath's proximal section; and FIG. 6 is a cross-sectional view of the distal ends thereof.

DESCRIPTION OF THE PREFERRED EMBODIMENT OF THE INVENTION

Referring now to the drawing, there is shown in FIG. 1 a syringe and needle assembly 1 wherein an hypodermic needle 2 which is shown penetrating the epiderm 3 of a patient is equipped with a retractable sheath 4 illustrated in an almost complete retracted position. The sheath comprises a frusto-conical base 5 which is internally dimensioned to intimately engage the hub 6 of the needle 2. The hub itself is connected to the outlet tip of the syringe 7. A collapsible sleeve 8 extends coaxially from the distal end 9 of the base around the cannula 10 of the needle and terminates in a constricted distal section 11 which has a much lesser cross diameter than the bulk of the collapsible sleeve 8. The entire sheath is formed from a resilient material in its expanded position so that after being compressed as shown in FIG. 1 as the needle penetrates the patient's body, it will automatically spring back and cover the entire needle as it is withdrawn from the body.

The construction of this first embodiment of the sheath 4 is better illustrated in FIGS. 2-4.

The sheath 4 has a length commensurate with the length of the cannula 10 of the needle, except for the terminal tip section 11 which extends beyond the pointed end 12 of the cannula. The base 5 is substantially frusto-conical with a coaxial opening 13 in the proximal end which is commensurate with the diameter of the proximal half section 14 of the needle hub 6. Since the hubs of a large majority of medical needles are substantially conical, a universally sized base 5 can adaptably engage over the hubs of a wide range of medical needles of various sizes. Four semi-circular tunnels 14 on the periphery of the base 5 extend almost the entire length of the base, tapering down slightly toward its distal end 9. The tunnels 14 serve two purposes. First, they facilitate expansion of the diameter of the base 5 when it is forceably engaged over the conical hub 6. Secondly, the inner channels 15 defined by the tunnels provide an escape for the air when the sheath is retracted. The bellowed main body of the sheath 4 is formed by alternately inverted frusto-conical sections 16 and 17 which are joined along inner folding ring sections 18 and outer folding ring sections 19. The inner and outer folding ring sections 18, 19 are formed integrally with the frusto-conical section 16, 17 during the molding process, and in the extended bellows position illustrated in FIG. 2. The entire sheath is made from a preferably transparent resilient material. Accordingly, if the sleeve 8 is retracted or collapsed toward the base 5 it will bounce back to its extended relaxed or resting position illustrated in FIG. 2. The material may be selected from a group of resins such as polyethylene terepehalate suitable for medical applications.

In this first embodiment, the successive alternately inverted frusto-conical sections 16, 17 and the walls are at a substantially same angle with the axis XX which is common to the sheath 4 and to the needle 2. This angle may be from 30 to 80 degrees. However, a slight widening of the bellows of one or two degrees away from the base 5 tends to favorize a more compact stacking of the compressed bellows as shown in FIG. 1, as the most distal ones extend over the proximally adjacent sections. The compacting effect may be improved by making their inverted frusto-conical sections 17 slightly shorter than the adjacent frusto-conical sections 16.

The top section 11 forms a generally elongated frusto-cone about an axis YY which is parallel but slightly offset from the axis XX of the sheath and needle. About three-quarters of the periphery of the tip 11 is indented with a series of crescent-shaped wedges 20 of progressively diminishing radius. The top and bottom converging walls 21, 22 of each indentation are positioned in axially alignment with the cannula 10 when the sheath is in its relaxed position. If the sheath is axially retracted, the pointed tip 12 of the needle would have to perforate up to ten layers of material, that is, go through all the crescent-shaped converging walls 21, 22 before exiting beyond the tip section 11. However, the cannula 10 will emerge beyond the distal end 23 of the tip section 11 if that section is slightly tilted or shifted to engage the pointed end 12 into the channel 24 constituted by the non-indented portion of the tip section 11. This can be accomplished by first contacting the area of the patient's skin which must be penetrated by the needle at the slight oblique angle with the distal end 23 and maneuvering the needle tip 12 through the channel 24 as the needle is being thrust axially forward. This maneuver is greatly facilitated by the transparency of the sheath. Alternately, the median section of the sheath can be manually withdrawn or retracted until the pointed end 12 of the needle is engaged into the channel 24 before thrusting the needle through the patient's epiderm.

A second embodiment of the invention is illustrated in FIGS. 5 and 6. The differences with the just-described first embodiment resides in the treatment of the base and most proximal bellows sections. In this second embodiment, the base 25 is substantially similar to the base 5 of the previous embodiment except that the bellows sections are not attached to the distal end 26 but to the periphery of the proximal end 27. The frusto-conical sections 28 of the bellows which surround the base 25 have inner ring sections with a diameter approximately corresponding to the outer diameter of the median area 29 of the base 25. Furthermore, the inverted frusto-conical sections 30 are slightly shorter than the non-inverted adjacent sections 31. The outer ring sections 33 are beaded and axially grooved to allow folding at a very acute angle without breaking of the material. Only a limited number of bellows sections are so configured. The remainder and bulk of the bellows sections 33 are similar in construction as the bellows sections of the first embodiment. As the most proximal bellows sections are tightly folded in an overlapping configuration 34, the inner folding rings 35, as they move axially around the base 25 come in contact with the outer wall 36 of the base and become jammed against it effectively locking the proximal bellows sections into the collapsed configuration 34. The overall length of the sheath 4 can thus be adjusted until the pointed end 12 of the needle is engaged into the channel 24 of the tip section 11 which is constructed and offset as in the previous described embodiment. Once caught in this position, the needle and sheath are ready for thrusting into the patient's body without further manipulation. Once the needle is withdrawn from the patient's body, the sheath will automatically expand under its own resiliency with enough inertia to unlock at least one proximal bellows section so that the pointed end 12 of the needle will be completely covered and safely shielded behind the indented tip section 11. In the event that the pointed end 12 of the needle remains engaged into the tip section 11 as shown in FIG. 6, a pinching pressure applied to any part of the bellows section will radially collapse it at least one of such sections, thus further expanding the sheath to dislodge the pointed end 12 of the needle from the channel 24 and prevent accidental retraction of the sheath.

While the preferred embodiments of the invention have been described, modifications can be made and other embodiments may be devised without departing from the spirit of the invention and the scope of the appended claims.

What is claimed is:

1. In combination with an injecting needle having a rigid cannula extending from a coaxial hub for connecting to the outlet of a syringe or the like to a pointed distal tip, a retractable sheath which comprises:
   a hollow base shaped and dimensioned to intimately engage over the hub;
   a sleeve extending coaxially from the base around the length of the cannula, said sleeve being formed by a plurality of alternately inverted frusto-conical segments joined by resiliently pliable alternating inner and outer ring sections;
   wherein said alternately inverted frusto-conical segments and ring sections are integrally molded from a common resilient material; and
   wherein said sleeve comprises an end portion having a substantially lesser cross-sectional diameter than the major part of the sleeve.

2. The combination of claim 1, wherein said end portion extends beyond the distal tip of the cannula when the sleeve is in said resting position.

3. The combination of claim 2, wherein said end portion lies about an axis substantially parallel and spaced apart from the axis of the needle and sleeve.

4. The combination of claim 3, wherein a succession of contiguous frusto-conical segments have alternating long and short heights.

5. The combination of claim 1, wherein said sleeve extends coaxially from the proximal end of and around said base.

6. The combination of claim 5, wherein said succession of contiguous segments surround said base.

7. The combination of claim 5, wherein the outer ring sections joining said succession of contiguous segments are beaded and internally grooved to facilitate folding.

8. In combination with an injecting needle having a rigid cannula extending from a coaxial hub for connecting to the outlet of a syringe or the like to a pointed distal tip, a retractable sheath which comprises:
   a hollow base shaped and dimensioned to intimately engage over the hub;
   a collapsible sleeve resiliently biased to extend coaxially from the base around the length of the cannula in a rest position;

said sleeve comprising a distal end portion having a substantially lesser cross-sectional diameter than the major part of the sleeve, and extending beyond the distal tip of the cannula when the sleeve is in said rest position; and wherein said end portion lies about an axis substantially parallel and spaced apart from the axis of the needle and sleeve.

9. In combination with an injecting needle having a rigid cannula extending from a coaxial hub for connecting to the outlet of a syringe or the like to a pointed distal tip, a retractable sheath which comprises:

a hollow base shaped and dimensioned to intimately engage over the hub;

a collapsible sleeve extending coaxially from the base around the length of the cannula, said sleeve comprising a distal end portion having a substantially lesser cross-sectional diameter than the major part of the sleeve, and extending beyond the distal tip of the cannula;

said end portion lying about an axis substantially parallel and spaced apart from the axis of the needle and sleeve; and wherein said end portion comprises a plurality of indentations projecting across the axis of the needle and sleeve.

* * * * *